United States Patent [19]

Randall

[11] Patent Number: 5,405,353
[45] Date of Patent: Apr. 11, 1995

[54] MICROSURGICAL NEEDLE HOLDER

[76] Inventor: Peter Randall, Tenth Floor/Penn Tower, 3400 Spruce St., Philadelphia, Pa. 19104

[21] Appl. No.: 164,044

[22] Filed: Dec. 8, 1993

[51] Int. Cl.⁶ ............................................. A61B 17/00
[52] U.S. Cl. ..................................... 606/147; 606/210
[58] Field of Search .............................. 606/205–211, 606/144–148, 51, 52; 294/99.2; 128/751; 81/43

[56] References Cited

U.S. PATENT DOCUMENTS

| | | |
|---|---|---|
| 253,209 | 2/1882 | Jones . |
| 2,523,932 | 9/1950 | Abbott ............................... 294/99.2 |
| 4,165,745 | 8/1979 | Heifetz . |
| 4,414,908 | 11/1983 | Eguchi et al. . |
| 4,446,866 | 5/1984 | Davison . |
| 4,753,235 | 6/1988 | Hasson . |
| 4,825,864 | 5/1989 | Hariri . |
| 4,873,979 | 10/1989 | Hanna ................................ 606/210 |
| 4,898,157 | 2/1990 | Messroghli et al. . |
| 4,938,214 | 7/1990 | Specht et al. . |
| 4,961,742 | 10/1990 | Torre . |
| 4,994,061 | 2/1961 | McPherson . |
| 4,994,079 | 2/1991 | Genese et al. . |
| 5,035,701 | 7/1991 | Kabbara . |
| 5,141,517 | 8/1992 | Shutt . |
| 5,159,861 | 11/1992 | Anderson . |

FOREIGN PATENT DOCUMENTS

| | | | |
|---|---|---|---|
| 0575804 | 4/1958 | Italy ...................................... | 606/210 |
| 2120593 | 12/1983 | United Kingdom . | |

Primary Examiner—Stephen C. Pellegrino
Assistant Examiner—William W. Lewis
Attorney, Agent, or Firm—Panitch Schwarze Jacobs & Nadel

[57] ABSTRACT

A microsurgical needle holder, including first and second elongate members pivotally hinged at their proximal ends and an intermediate member attached to the first elongate member intermediate its ends, and between the first and second members, has a slide and lock actuator for moving the first and intermediate members between a first position wherein the distal ends are spaced apart and a second position wherein the distal ends are engaged, so that a needle can be securely held therebetween. The needle holder can be hand held and the actuator fingertip controlled.

11 Claims, 2 Drawing Sheets

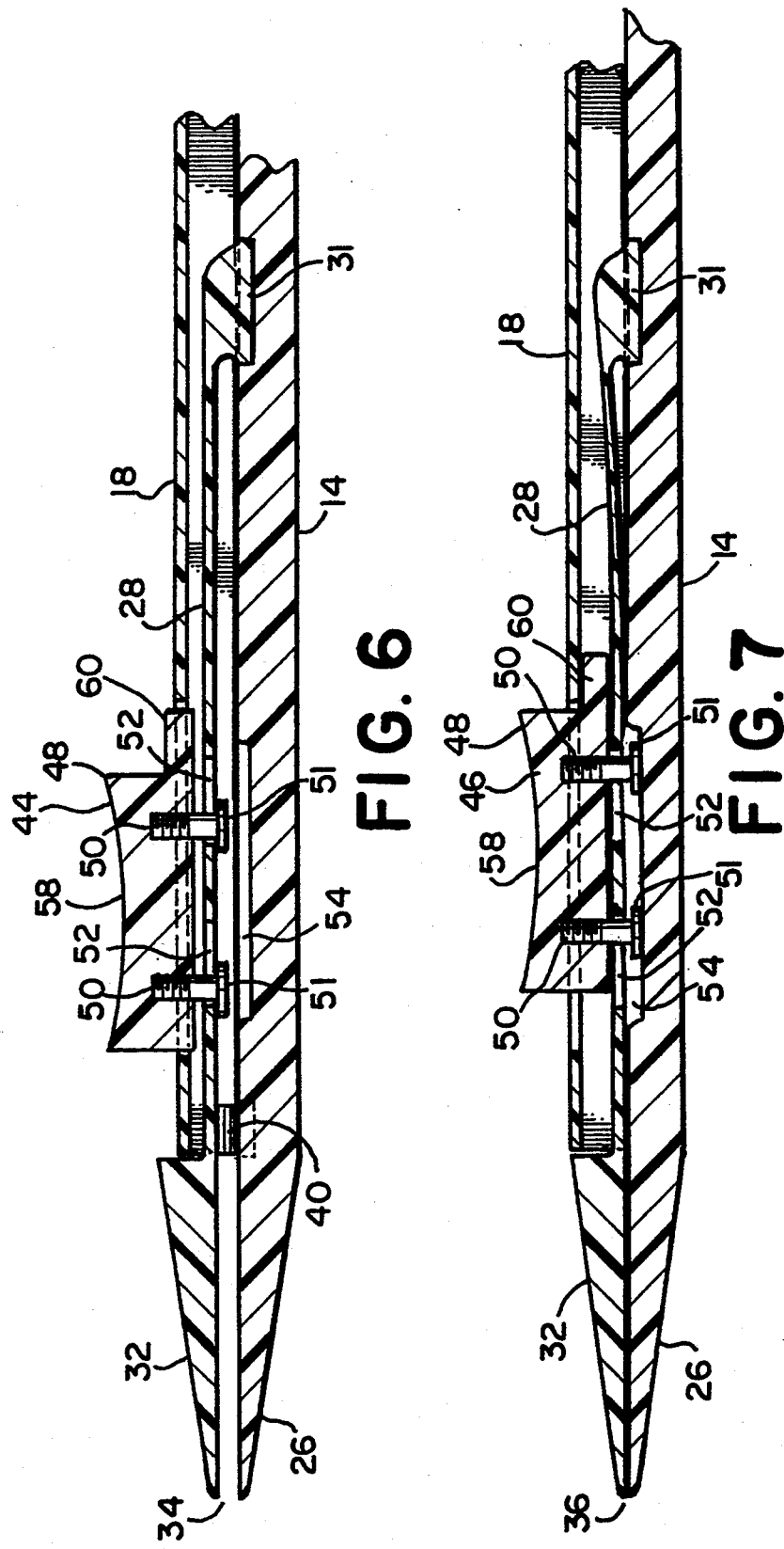

MICROSURGICAL NEEDLE HOLDER

FIELD OF THE INVENTION

The present invention relates to surgical equipment and, more particularly, to a hand-held, surgical needle holder.

BACKGROUND OF THE INVENTION

Microsurgery requires very small and very precise instruments, capable of being held and manipulated in a very precise manner for extended periods of time. Thus, these instruments must be comfortable to hold and relatively easy to manipulate to compensate for a user's hand fatigue.

Needle holders for use in microsurgery are known. There are generally two types of such needle holders. The first type has two arms pivotally connected between their distal and proximal ends, with the proximal side of the pivot forming handles and the distal side of the pivot forming jaws. This type of needle holder operates like a pair of pliers, that is, when the handles are moved toward each other, the jaws close, and vice versa. A needle holder of this type is disclosed in U.S. Pat. No. 4,898,157. This type of needle holder requires a hand motion far more gross than fingertip control so that under microscopic conditions, it is difficult to hold the jaws steady.

The second type of needle holder is of the tweezers type. This design has two arm members connected at their proximal ends. Jaws are formed at the distal ends and are activated by pressing the two arms together. A locking mechanism is usually included to hold the arms together in a closed position. A needle holder of this type is disclosed in U.S. Pat. No. 4,938,214. One drawback with this type of needle holder is that the tweezer action can be unstable due to the fact that the instrument is held between only two fingers (thumb and index). While this instrument is easier to hold steady than the pliers-like instrument, it lacks the control afforded by an instrument which may be manipulated using three fingers.

The present invention provides a microsurgical needle holder design which is a novel variation of the second design, thus providing a needle holder which is very precise, yet simple and may be comfortably held and manipulated for extended time periods.

SUMMARY OF THE INVENTION

Briefly stated, the present invention comprises a microsurgical needle holder having a first elongate member with a proximal end and a distal end, a second elongate member with a proximal end and a distal end, and an intermediate member having a proximal end and a distal end. The second member is secured to the first member, and the intermediate member proximal end is affixed to the first member intermediate to the first member ends. The intermediate member is movable between a first position where the intermediate member distal end is spaced from the first member distal end, and a second position where the intermediate member distal end and the first member distal end are in engagement. A locking actuator member is slidably disposed on the intermediate member, and is movable between a release position and a locked position. In the release position, the intermediate member distal end is in its first position, and in the locked position, the intermediate member distal end is in its second position. When the intermediate member is in its second position, a microneedle can be held between the first member and the intermediate member distal ends.

BRIEF DESCRIPTION OF THE DRAWINGS

The foregoing summary, as well as the following detailed description of a preferred embodiment of the present invention will be better understood when read in conjunction with the appended drawings. For the purpose of illustrating the invention, there is shown in the drawings, an embodiment which is presently preferred. It should be understood, however, that the present invention is not limited to the particular arrangement and instrumentality shown. In the drawings:

FIG. 6 is an enlarged partial cross-sectional view of the microsurgical needle holder of FIG. 1., taken along lines 6—6 of FIG. 2, in a release position; and FIG. 7 is a partial cross-sectional view of the microsurgical needle holder of FIG. 6, in a locked position.

DETAILED DESCRIPTION OF THE INVENTION

Certain terminology is used in the following description for convenience only and is not limiting. The words "inwardly" and "outwardly" refer to directions toward and away from, respectively, the geometric center of the microsurgical needle holder and designated parts thereof. The terminology includes the words above specifically mentioned, derivatives thereof and words of similar import.

Figure 1:
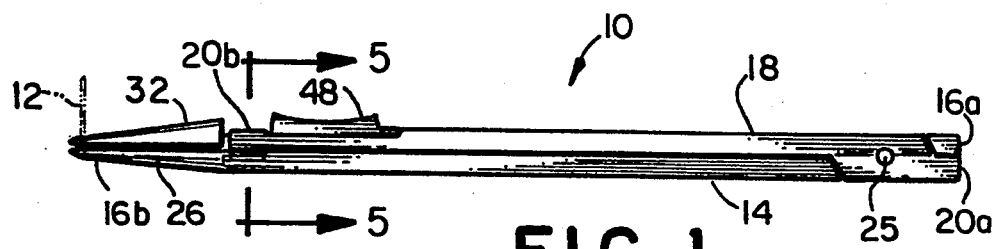
FIG. 1 is a side elevational view of a microsurgical needle holder in accordance with the present invention.
Figure 2:
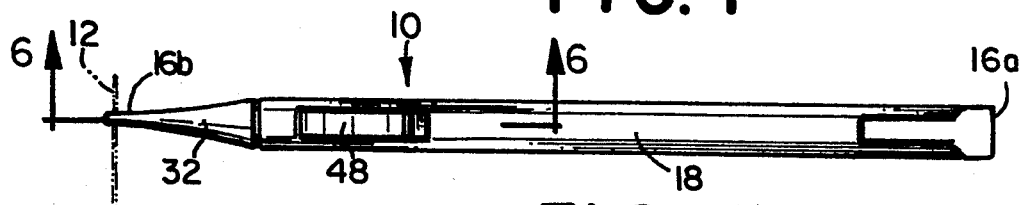
FIG. 2 is a top plan view of the microsurgical needle holder of FIG. 1.
Figure 3:
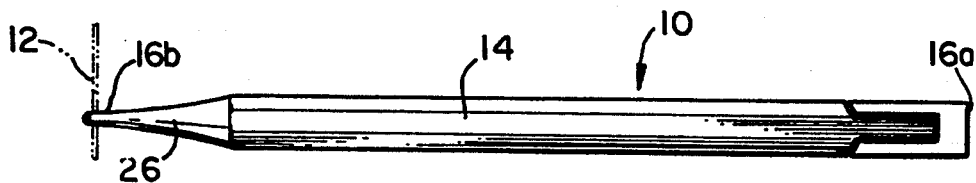
FIG. 3 is a bottom plan view of the microsurgical needle holder shown in FIG. 1.
Figure 4:
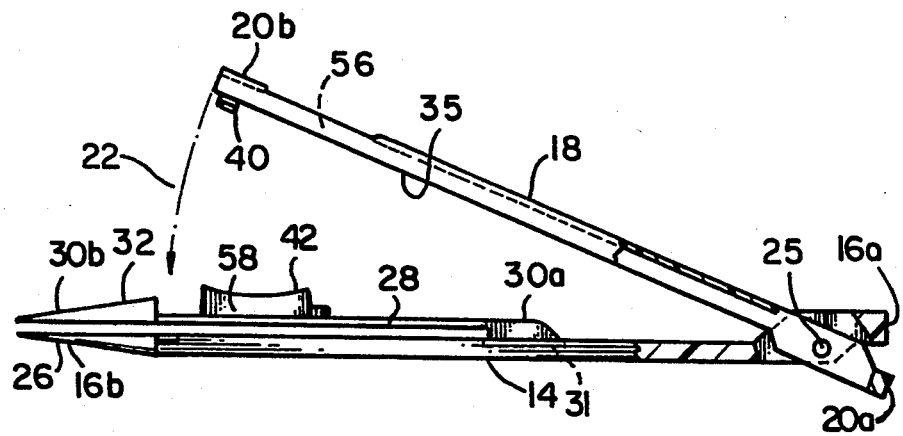
FIG. 4 is a side elevational view of the microsurgical needle holder of FIG. 1. shown in an open position.

Referring to the drawings in detail, wherein like numerals indicate like elements throughout, there is shown in FIGS. 1 through 7 a preferred embodiment of a microsurgical needle holder, generally designated 10, for holding a microsurgical needle 12 (shown in phantom) in accordance with the present invention. FIGS. 1 and 4 are side elevational views of the needle holder 10. The needle holder 10 includes a first elongate member 14 having proximal end 16a and distal end 16b, and a second elongate member 18, having proximal end 20a and distal end 20b. As shown in FIG. 4, in the preferred embodiment, the first member 14 and the second member 18 are hinged at their proximal ends 16a, 20a, for pivotal or arcuate movement between an open position 22 (FIG. 4) and a closed position 24 (FIG. 1). In the open position 22, the distal end 16b of the first member 14 is spaced apart from the distal end 20b if the second member 18 and in the closed position 24, the distal ends 16b, 20b are in proximate relation. FIG. 4 shows the first and second members 14, 18 in the open position 22, while FIGS. 1-3 and 5-7 show the first and second members 14, 18 in the closed position 24. The members 14, 18 may be connected or hinged at their proximal ends 16a, 20a by means of a pin 25 which extends through suitably sized and aligned openings in the proximal ends 16a, 20a of the two members 14, 18. Additionally, the proximal ends 16a, 20a may be formed like a clevis or otherwise cut and bevelled to facilitate connecting the members 14, 18 by the pin 25. If desired, the members could be connected together for pivotal movement in some other manner.

Although the first member 14 and the second member 18 are hinged in the preferred embodiment, it is also envisioned that the two members 14, 18 could be integrally connected or formed together to establish a single, generally continuous housing (not shown) if desired. Members 14 and 18 could be integrally constructed of an injection-molded, high strength plastic material. This may be desired if a disposable unit is manufactured, requiring lesser functionality and lower manufacturing costs.

In the present embodiment, elongate members 14, 18 are in the form of two similarly shaped half sections which are preferably constructed of surgical or stainless steel. As is well known, reusable surgical instruments are often constructed from surgical or stainless steel because these materials are readily sterilized using an autoclave. Needle holder 10, however, may also be constructed using any other metal or metal alloy, plastic, or composite material which is suitable for surgical instruments, such as titanium.

As is apparent from FIG. 4, the first member 14 is of greater length than second member 18. The needle holder 10 is designed to be approximately the same overall size and generally the same six-sided shape of a standard wood pencil, so that it may be comfortable and familiar to hold, and of good balance. It is also equally adaptable for use by either a right- or left-handed surgeon or other user. Thus, the first elongate member 14 is generally about 6 inches long and the second elongate member 18 is generally about 5 inches long, although these lengths and the variations therebetween may differ. The difference in lengths between the two members 14, 18 comprises the length of a first microneedle holder tip 26, located at the distal end 16b of the first elongate member 14.

Figure 5:
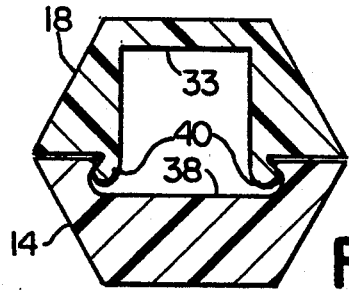
FIG. 5 is an enlarged partial cross-sectional view of the microsurgical needle holder of FIG. 1., taken along lines 5—5 of FIG. 1.

First and second members 14, 18 are shaped and adapted to mate with each other when in the closed position 24 (FIG. 1). As best shown in FIG. 5, the elongate members 14, 18, when in proximate relation, give the needle holder 10 a generally hexagonal cross-sectional shape. The precise shape of the needle holder 10 has advantages in that it is equally conducive to both left-hand and right-hand use. Additionally, the pencil shape provides three flat surfaces for grasping, using a design that is as familiar as a wooden pencil, is natural, and well balanced.

However, the needle holder 10 may be of any conventional shape conducive to being comfortably hand-held, such as the shape of a pen or pencil, or other such hand-held tool or implement. Thus other external geometric cross-sectional characteristics are within the spirit and scope of the invention, such as cylindrical, square, or rectangular.

An intermediate member 28, having a proximal end 30a and a distal end 30b is affixed at its proximal end 30a to the first member 14 at a point 31 intermediate to first member ends 16a, 16b. In order to accommodate the intermediate member 28 when the needle holder 10 is in the closed position 24, the second elongate member 18 has an open channel or groove 33 which runs along its underside (FIG. 5). As is readily apparent from FIG. 4, the distal end 30b of the intermediate member 28 extends beyond the distal end 20b of the second member 18, in the same manner as the first elongate member distal end 16b extends beyond the second member distal end 20b. The distance which the intermediate member distal end 30b extends beyond the second elongate member distal end 20b comprises a second microneedle holder tip 32 which is complementary to holder tip 26.

Microneedle holder tips 26, 32 are designed to securely hold the microsurgical needle 12 when in close proximate relation. As shown in FIGS. 1-3, the microsurgical needle 12 is usually curved and is usually held at a 90 degree angle with respect to a longitudinal axis of the microsurgical needle holder 10.

Although microsurgical needle holder tips 26, 32 are shown as integral to the first member 14 and the intermediate member 26, respectively, it is envisioned that the tips 26, 32 could also comprise separate attachments, which vary in size and shape, as desired to hold a needle or similar instrument at various angles. The microsurgical needle holder tips 26, 32 may also be designed to be removable elements which can be disposable.

The intermediate member 28 is movable between a first position 34 (FIG. 6) wherein the intermediate member distal end 30b is spaced from the first elongate member distal end 16b and the holder tips 26, 32 are separated, and a second position 36 (FIG. 7) wherein the intermediate member distal end 30b and the first elongate member distal end 16b are in engagement and the holder tips 26, 32 are in engagement with each other. In the second position 36, the microsurgical needle 12 is enclosed between the microsurgical needle holder tips 26, 32, (FIGS. 1-3) and held securely therebetween.

Intermediate member 28 is constructed of a flexible material, such as spring steel in the preferred embodiment, and is formed and shaped so that it is naturally biased away from the first elongate member 14 and into the first position 34. The pressure required to move the intermediate member 26 against the bias and into the second position 36 is minimal so that it can be easily moved from the first position 34 to the second position 36 by the user. On the other hand, the biasing force is strong enough to maintain the intermediate member 28 in the first position 34 when no force is exerted thereupon.

The intermediate member 28 may be attached to the first elongate member 14 in any convenient manner. For instance, the intermediate member 28 could be soldered, welded, or glued to the surface of the first elongate member 14, or a notch, bevel, or opening could be placed in the surface of the first elongate member 14 in which the intermediate member proximal end 30a could be secured. Additionally, the intermediate member 28 could be riveted or screwed to the first elongate member 14.

A connecting member is provided to releasably secure the microneedle holder 10 in the closed position 24. The second elongate member distal end 20b is adapted to mate to the first elongate member 14 proximate to the first microneedle holder tip 26. The connecting member is in the form of a snap-lock member. The first elongate member 14 has a notched snap-lock recess 38 (FIG. 5) disposed proximate to its distal end 16b which is adapted to receive and hold two corresponding spaced apart snap-lock flanges 40 disposed on the second elongate member distal end 20b. Thus, when the needle holder 10 is placed in the closed position 24, the notches 40 are pressed into and snap fitted within the grooved recess 38 in the first elongate member 14, to releasably hold the second member 18 in the closed position 24 whereby the needle holder may be comfortably held and easily manipulated by the user or opened as in FIG. 4 for cleaning.

A locking actuator member 42 is slidably disposed on the surface or periphery of the intermediate member 28 between the intermediate member ends 30a, 30b for movement between a release position 44 (FIG. 6) wherein the intermediate member distal end 30b is in the first position 34, and a locked position 46 (FIG. 7) wherein the intermediate member distal end 30b is in the second position 36, whereby a microsurgical needle 12 can be held and locked between the microsurgical needle holder tips 26, 32. The locking actuator member 42 functions to move the microsurgical needle holder tips 26, 32 between the first position 22 and the second position 24. Thus, when the actuator member 42 is in the release position 44, the needle holder 10 is in the first position 34, and when the actuator member 42 is in the locked position 46, the needle holder 10 is in the second position 36.

In the preferred embodiment, the locking actuator member 42 comprises a generally rectangular shaped button 48 slidably disposed on the surface of the intermediate member 28. The button 48 has one or more perpendicular projections 50 which extend from the button 48 through one or more corresponding elongate apertures 52 in the intermediate member 28, and into a channel 54 in the first elongate member 14. The first elongate member channel 54 is positioned between the grooved recess 38 and the point 31 where the intermediate member 28 is secured to the first elongate member 14. In the preferred embodiment, the projections 50 are screws with screw-heads 51 which slide in the first elongate member channel 54, screw shanks which project through the intermediate member apertures 52, and screw threads which are secured in the button 48. Although the presently preferred embodiment uses screws for projections 50, it should be understood by those skilled in the art that other suitable projection means may be used, such as rivets, nails or tacks.

When the needle holder 10 is in the closed position 24, the button 48 protrudes through an opening or aperture 56 in the second elongate member 18, so that the button 48 is accessible by the surgeon or other user. The button 48 has an engagement surface 58 adapted for engagement of a finger or thumb of a surgeon or other user for actuation thereof. The engagement surface 58 includes a shallow recess, generally in the shape of an oval, for enhancing grasping characteristics. The engagement surface 58 may be knurled, roughened, or otherwise treated to further enhance the grasping characteristics thereof.

Additionally, the button 48 has a tab 60 on its proximal side which projects outwardly from the engagement surface 58. When the button 48 is pressed toward the first elongate member 14, and moved toward the first member proximal end 16a, the screw heads 51 travel through channel 54, and the tab 60 is moved into a position between the second member 18 and the intermediate member 28, where the button 48 is held in place by the pressure forces exerted on the tab 60. Thus, in the locked position, the button is releasably fixed to the second elongate member 18. By pressing the button 48 toward the first member 14, the intermediate member 28 may be moved into the second position 36, whereby a microsurgical needle 12 may be securely held between the microsurgical needle holder tips 26, 32, and by sliding the button 48 toward the proximal ends 16b, 20b, the button may be moved into the locked position 46, whereby the tab 60 on the button 48 is firmly held between the intermediate member 28 and the second elongate member 18 and the needle 12 is firmly held between holder tips 26, 32. The needle holder 10, having button 48, is easily fingertip controlled for movement between the release position 44 and the locked position 46 so that needles of varying size and shape may be quickly and easily removed and inserted therebetween without requiring the user to change his grip on the needle holder 10.

Some users prefer not to have a locking mechanism as just described. The locking mechanism can be inactivated by fixing the button 48 to the intermediate member 28. One method to achieve this is to replace the screws 51 with shorter screws (or other fixating devices) so that the button 48 is securely held against the intermediate member 28, thereby making it impossible to slide the button 48 from the release position 44 to the locked position 46.

From the foregoing description, it can be seen that the present invention comprises a microsurgical needle holder with a slide and lock button for releasing and engaging a needle. The pencil shape provides three flat surfaces for grasping and using a design that is as familiar as a wooden pencil, as natural and well balanced. Opening and closing the needle holder tips is accomplished by simply depressing the index finger as in squeezing a pencil harder and then releasing. Locking is accomplished by simply sliding the depressed button backwards without changing the grip. This is very important for the control and manipulation needed in microsurgery. In addition, it minimizes fatigue which is important in prolonged, tedious types of surgery, and further it is equally useful for right-handed and left-handed surgeons. Thus, the control and manipulation of the instrument are done completely by the fingertips using three points of contact, (i.e., thumb, index and middle fingers). Most other needle holders require either grasping the instrument at a distance from the tip, as in holding a pair of scissors. Then, the action of opening and closing the tips becomes a fairly gross one of squeezing the handles together. In a tweezer-like needle holder, the grip is between just the thumb and index finger which is far less stable than a three-point contact, as in the present invention.

It will be appreciated by those skilled in the art that changes and modifications may be made to the above described embodiment without departing from the inventive concept thereof. The present invention should not be limited to the particular embodiment disclosed, but it is intended to include all modifications and changes which are within the scope and spirit of the invention as defined by the appended claims.

What is claimed is:

1. A microsurgical needle holder comprising:
a first elongate member having a proximal end and a distal end;
a second elongate member having a proximal end and a distal end, said second member at said first member proximal end being secured to said first member;
an intermediate member having a proximal end and a distal end, said intermediate member proximal end being affixed to said first member intermediate said first member ends, wherein said intermediate member is movable between a first position wherein said intermediate member distal end is spaced from said first member distal end, and a second position wherein said intermediate member distal end and said first member distal end are in engagement; and a locking actuator member slidably disposed on said intermediate member, said actuator member being movable between a release position wherein said intermediate member distal end is in said first position, and a locked position wherein said intermediate member distal end is in said second position whereby a micro needle can be held between said first member and said intermediate member distal ends.

2. The microsurgical needle holder as recited in claim 1, wherein said actuator member comprises a button slidably disposed on said intermediate member and projecting through an aperture in said second member when said second member distal end is secured to said first member distal end, said button being movable between said release position wherein said button is movable with respect to said second member and said locked position wherein said button is releasably fixed to said second member.

3. The microsurgical needle holder as recited in claim 2, wherein when said button is moved from said release position to said locked position said button is first moved toward said first member to cause said intermediate member to move into said second position, and said button is then slid toward said proximal ends into locking engagement with said second member to hold said intermediate member in said second position.

4. The microsurgical needle holder as recited in claim 1, wherein said intermediate member is constructed of a flexible material and is biased away from said first member.

5. The microsurgical needle holder as recited in claim 4, wherein said intermediate member is constructed of spring steel.

6. The microsurgical needle holder as recited in claim 1, wherein said first and said second members are hinged at their proximal ends for arcuate movement between an open position wherein said first and said second member distal ends are in spaced apart relation and a closed position wherein said first and said second member distal ends are in proximate relation.

7. The microsurgical needle holder as recited in claim 6, further comprising a connecting member releasably securing said second member to said first member when in said closed position.

8. The microsurgical needle holder as recited in claim 7, wherein said connecting member comprises a snap-lock member on said second member for engagement with a snap-lock recess on said first member when said first and second members are in said closed position.

9. The microsurgical needle holder as recited in claim 8, wherein said snap-lock member comprises two spaced apart flanges affixed to said second member and said snap-lock recess comprises a complementary notched recess on said first member receiving said flanges when said first and said second members are in said closed position.

10. The microsurgical needle holder as recited in claim 1, wherein said second member is formed integral to said first member.

11. A microsurgical needle holder comprising:
a first elongate member having a proximal end and a distal end;

a second elongate member having a proximal end and a distal end, said second member being hinged to said first member at their proximal ends for arcuate movement between an open position, wherein said first and said second member distal ends are in spaced apart relation, and a closed position, wherein said first and said second member distal ends are in proximate relation;

an intermediate member constructed of a flexible material having a proximal end and a distal end, said intermediate member proximal end being affixed to said first member intermediate said first member ends, wherein said intermediate member is movable between a first position wherein said intermediate member distal end is spaced from said first member distal end, and a second position wherein said intermediate member distal end and said first member distal end are in engagement, wherein said intermediate member is normally biased away from said first member;

a locking actuator member slidably disposed on said intermediate member and projecting through an aperture in said second member when said second member distal end is proximate to said first member distal end, said actuator member being movable between a release position wherein said intermediate member distal end is in said first position, and a locked position wherein said intermediate member distal end is in said second position whereby a micro needle can be held between said first member and said intermediate member distal ends; and a connecting member releasably securing said second member to said first member when in said closed position, said connecting member comprising a snap-lock member on said second member for engagement with a snap-lock recess on said first member when said first and second members are in said closed position, said snap-lock member comprising two spaced-apart flanges affixed to said second member and said snap-lock recess comprising a complementary notched recess on said first member for receiving said, flanges when said first and said second members are in said closed position.

* * * * *